United States Patent [19]

Moulet

[11] 4,001,801
[45] Jan. 4, 1977

[54] AUTOMATIC LOW THROUGHPUT METERING APPARATUS FOR SELECTING AND CONTROLLING THE FLOW RATE OF LIQUIDS

[75] Inventor: Camille Moulet, Le Cannet, France

[73] Assignee: Crinospital S.p.A., Palazzo Pignano, Italy

[22] Filed: Nov. 19, 1974

[21] Appl. No.: 525,063

[30] Foreign Application Priority Data

Nov. 21, 1973  Italy .................. 31502/73

[52] U.S. Cl. .................. 340/239 R; 128/214 E; 128/DIG. 13; 137/487.5; 222/59
[51] Int. Cl.² .................. G08B 21/00
[58] Field of Search ........... 340/239 R; 128/214 E, 128/DIG. 13, 214 F; 222/59; 137/486, 487.5

[56] References Cited
UNITED STATES PATENTS

| 3,197,068 | 7/1965 | Corbin et al. ............ 222/59 |
| 3,623,052 | 11/1971 | Spiller ............ 340/239 R |

Primary Examiner—John W. Caldwell
Assistant Examiner—Daniel Myer
Attorney, Agent, or Firm—Finnegan, Henderson, Farabow & Garrett

[57] ABSTRACT

An automatic metering apparatus for selecting and controlling the flow rate of liquids, particularly for medical purposes, to be arranged between a liquid feeding container and a perfusion or transfusion line, comprises an electronic timer device capable of being pre-set from the outside in order to pre-select the flow rate of the liquid drops to be metered. A sequential electronic controlling circuit has its inputs connected to the outputs of the timer device, while its outputs control an actuator for causing liquid drops to inflow into the perfusion or transfusion line. An optic-electronic transducer is also provided for detecting the flow rate of the drops, the output of which is fed back to the input of the sequential circuit. The apparatus also comprises a counting device and at least one alarm device.

5 Claims, 5 Drawing Figures

AUTOMATIC LOW THROUGHPUT METERING APPARATUS FOR SELECTING AND CONTROLLING THE FLOW RATE OF LIQUIDS

BACKGROUND OF THE INVENTION

The present invention relates to an automatic metering apparatus for selecting and controlling the flow rate of liquids.

DESCRIPTION OF THE PRIOR ART

It is known that in several techniques and applications it is very important to be able to meter given quantities of liquid substances with high precision. For example it is much required in the medical field, where it is often necessary to rate and control the flowing of solution drops in a perfusion or transfusion fluid flow line.

However, completely automatic devices capable of affording such performances in a reliable manner, are as yet unknown.

SUMMARY OF THE INVENTION

The automatic liquid apparatus for liquid substances according to the invention, is adapted to be arranged between a liquid feeding container and a perfusion or transfusion line, and comprises an electronic timer device capable of being pre-set from the outside and adapted to pre-select the flow rate of the liquid drops to be metered; a sequential electronic controlling circuit, the inputs of which are connected to the outputs of said timing and pre-selecting circuit, and the outputs of which control an acutator means causing liquid drops to inflow into said perfusion line, a counting device and at least one alarm device; and an optic-electronic transducer for detecting the flow rate of the drops, the output of which is fed back to the input of said controlling sequential circuit.

DESCRIPTION OF THE PREFERRED EMBODIMENTS

Figure 1:
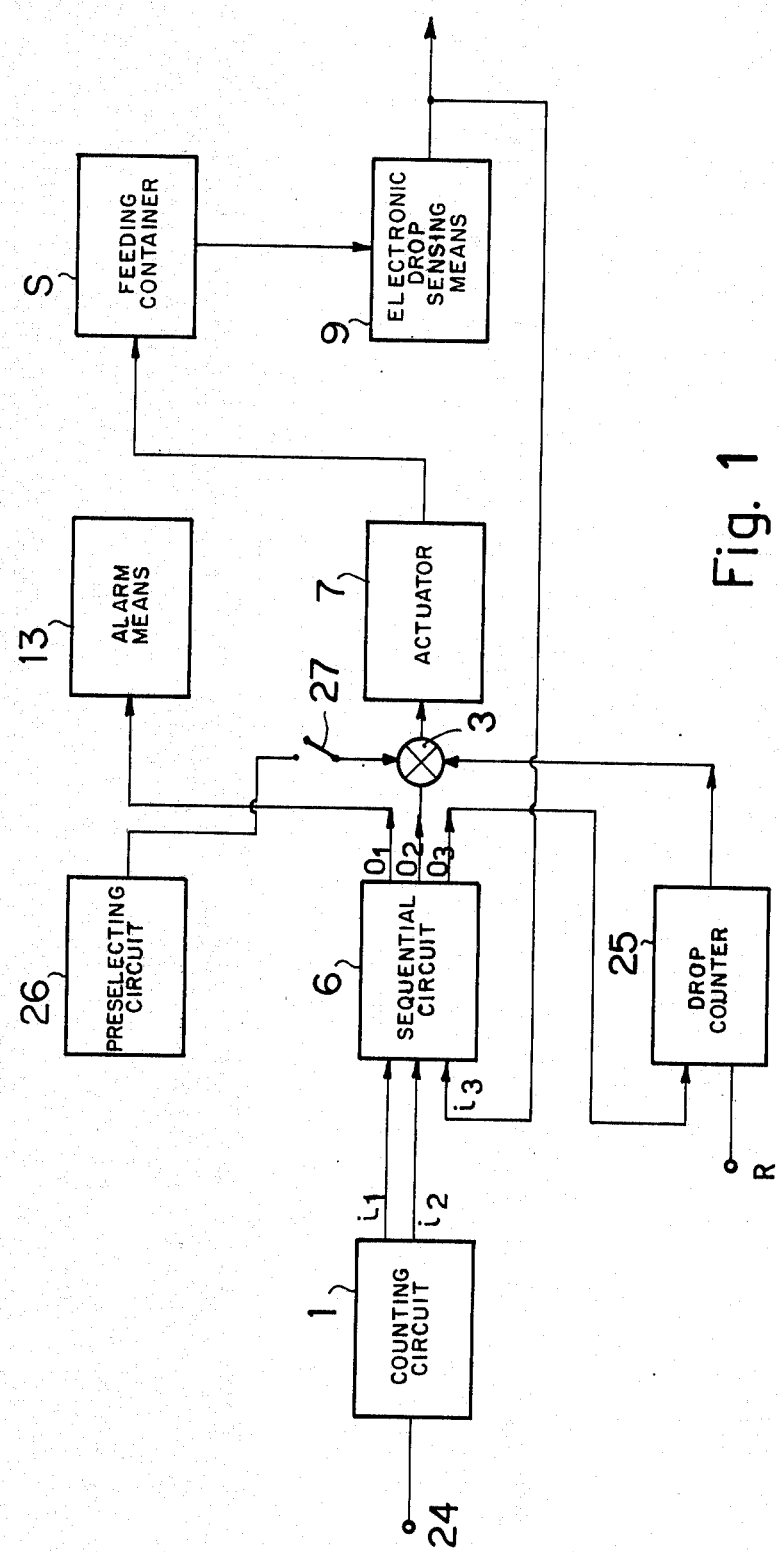
FIG. 1 is a block diagram of the main circuits in a metering apparatus according to the invention.

With reference to FIG. 1, a block 1 represents flow rate pre-selecting and timing circuits for a control circuit 6. More precisely, input $i_1$ gives a constant timing signal and input $i_2$ a flow rate signal which may be pre-set through manual action on a control panel of the apparatus (sliding contact 24 of FIG. 2). Output $o_2$ of the control circuit 6 is input to an actuator 7 through a comparator device 3; output $o_1$ is fed to alarm devices 13 and output $o_3$ is fed to a counter device 25 for counting the drops that have been fed.

The actuator 7, comprising a lever and a micro-valve, performs a demand of a drop of liquid from a vessel S. The outflow of such a liquid drop is detected by an optic-electronic transducer 9, the output of which is fed back to an input $i_3$ of the block 6. Before the actuator 7 is able to demand a drop of liquid, such a demand must be received from the output $o_2$ of the block 6 and the other two inputs of the comparator device 3 must not be equal, i.e the total number of drops required, which has been pre-set in a pre-selector 26, (possibly with the selector circuits inactivated by a switch 27) must not be equal to the total number of drops that has actually been fed and memorized by a device 25 having at its input the output $o_3$ of the circuit 6.

Furthermore, as the control circuit 6 receives at its input not only the timing signal $i_1$, but also the signals resulting from the desired flow rate and the actual flow rate at $i_2$ and $i_3$ respectively, the control circuit causes alarm circuits 13 to be activated, in the following cases:

a. if a continuous flow of drops is detected through input $i_3$. In this connection it is to be appreciated that a draining operation of the apparatus immediately actuates the alarm;

b. if a drop is fed without being requested by the signal at $i_2$;

c. if a drop is not fed when there is a demand:
1. at high flow rates, as the subsequent demand has arrived;
2. at low flow rates, after a given number of seconds have elapsed from its demand.

Besides signalling a possible failure and actuating the alarm 13, the circuit 6 causes the actuator 7 not to operate in any of the above described cases, unless the apparatus has been pre-set on the slider 14 for the "draining" operations.

With the above in mind, it should be clear that the alarms are also operated when the liquid container is empty, because the drop demand is not satisfied (point c above), as well as, upon detection of the required number of drops (pre-set on the selector 26) has been delivered because also in this case the drop demand is not satisfied, the actuator 7 being inoperative.

Figure 2:
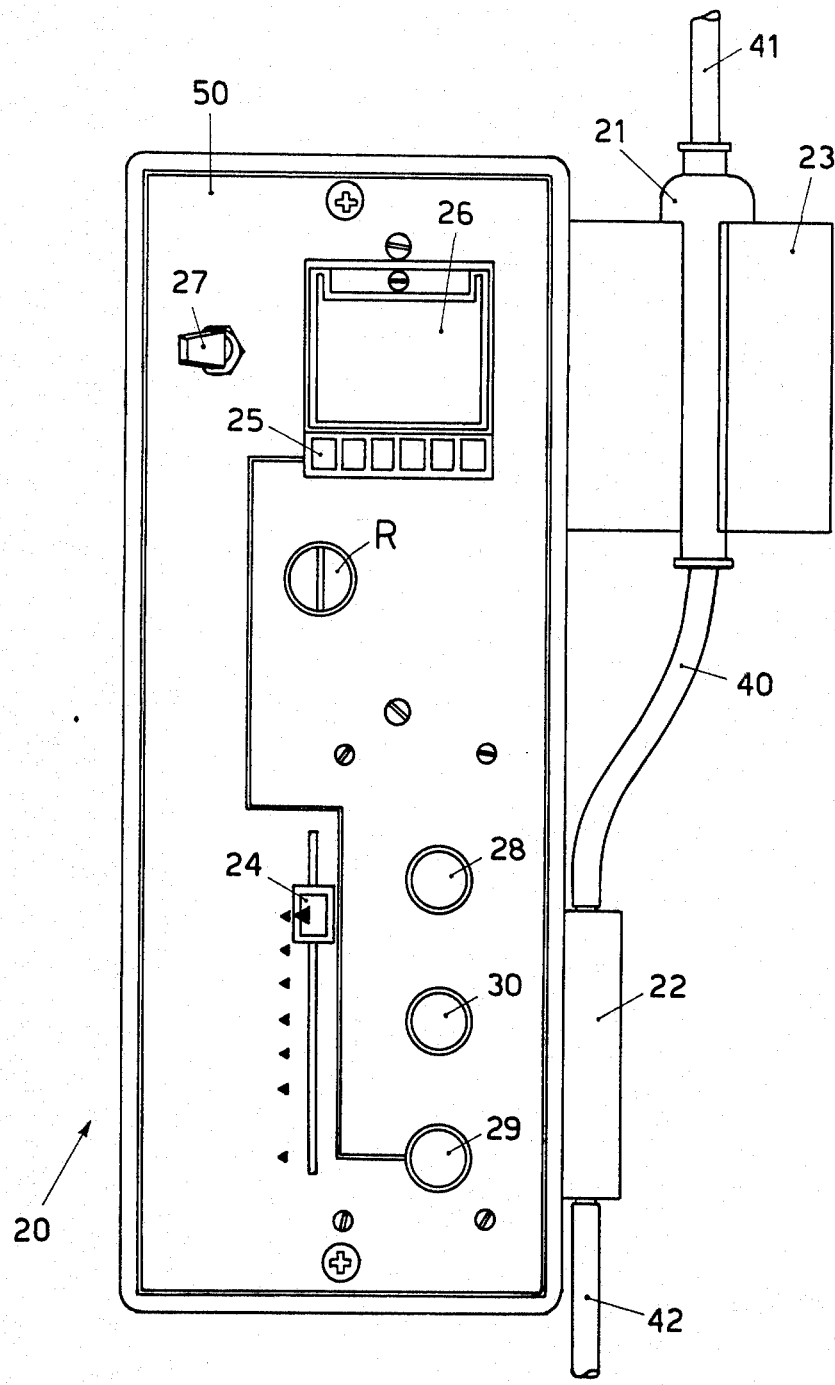
FIG. 2 is a front view of an external control panel of the apparatus.

FIG. 2 shows a front view of an instrument panel 50 according to a preferred embodiment of the apparatus generally indicated by numeral reference 20.

The apparatus as shown in FIG. 2 comprises a transparent vessel 21, a tube of plastic material 40, a switch 27, the digital selector 26, the counter 25 which displays the number of drops that have been fed, and which can be reset by a push-button R, the slider 24 for selecting the flow rate, three indicator lamps 28, 29, 30 (e.g. of green, yellow and red colours, respectively), a member 23 for housing and supporting the transparent vessel 21 and a side member 22, placed under the member 23, through which the tube 40 passes, and one end 41 of the tube is connected to the containers for feeding the liquid substance that is to be supplied, and the other end 42 is connected to a perfusion line or any utilization device or flowline. A panel 50 has on it all the necessary controls for the external pre-selection of the basic flow metering parmeters. Namely, the switch 27 has two stability positions, each of them corresponding, alternatively, either to energization or den-energization of the circuits of the selector 26.

The slider 24 can be moved to face any one of eight reference positions. The operative step corresponds to the highest position and the discharge or "draining" of the liquid to the lowest position. The six intermediate positions of the slider 24 represent different feeding flow rates. For example, the different positions could represent respectively flow rate metering of two, four, eight, sixteen, thirty-two, sixty-four drops per minute.

In addition to the choice of the feeding flow rate, the total number of drops that one desires to feed can be set by means of the pre-selector 26 actuated by the switch 27.

The counting and display device 25 on the contrary shows the number of drops that have been fed during the operation of the micro flow meter apparatus. Within the member 23, at the periphery of the surface in contact with vessel 21, there is provided an optic-electronic device (not shown) for detecting the drops as they fall through the vessel 21. More precisely, according to a preferred embodiment, the optic-electronic detector is adapted to emit an electro-magnetic radiation passing through the vessel 21. When a drop falls through the vessel, the radiation is partially caught and partially reflected by the drop itself, whereby the total energy travelling transversely throughout the vessel 21 is caused to vary, thus affording the possibility of counting the number of drops fed and measuring the actual feeding flowrate.

Figure 3:
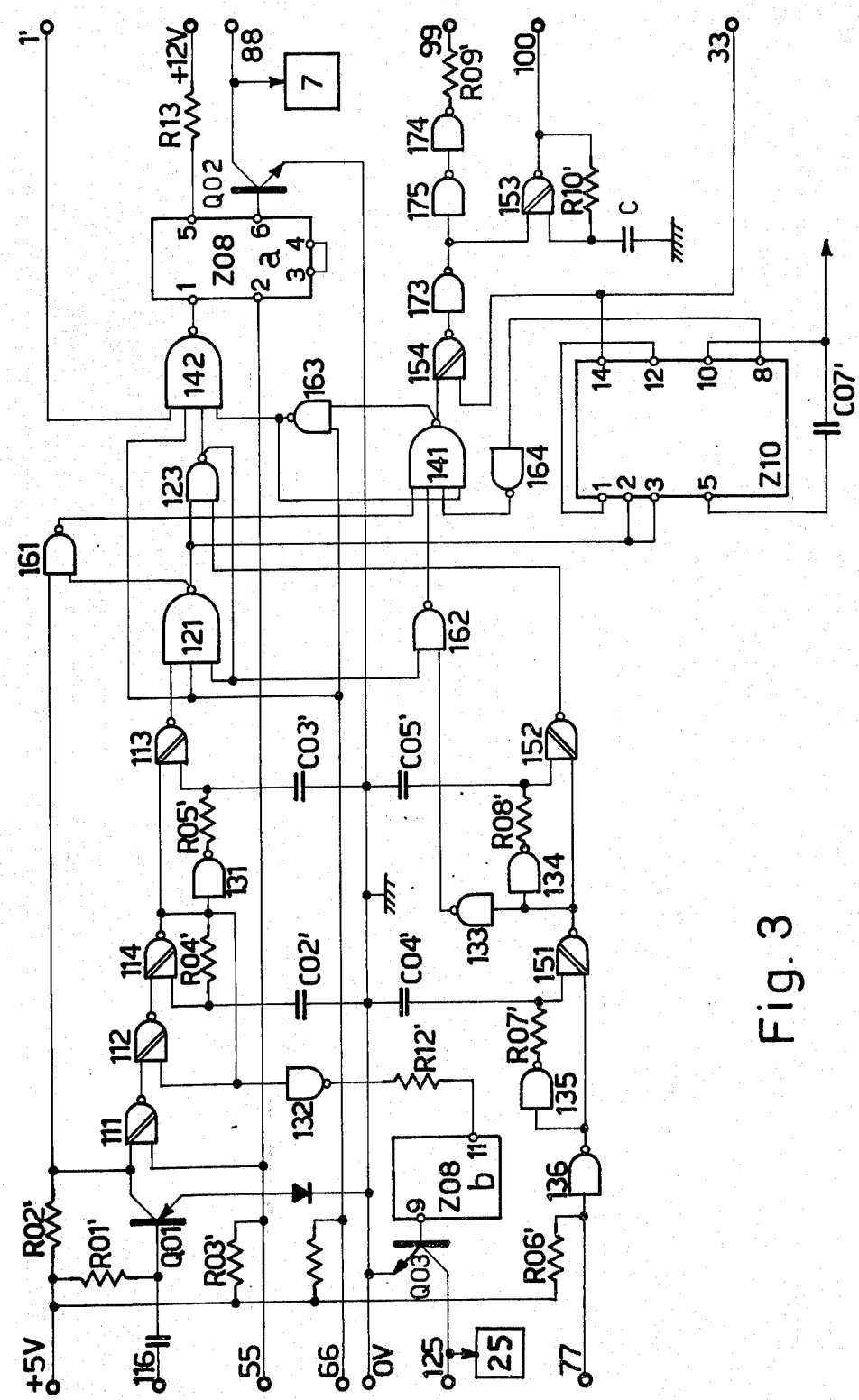
FIG. 3 shows a diagram of sequential control circuits of the apparatus.
Figure 4:
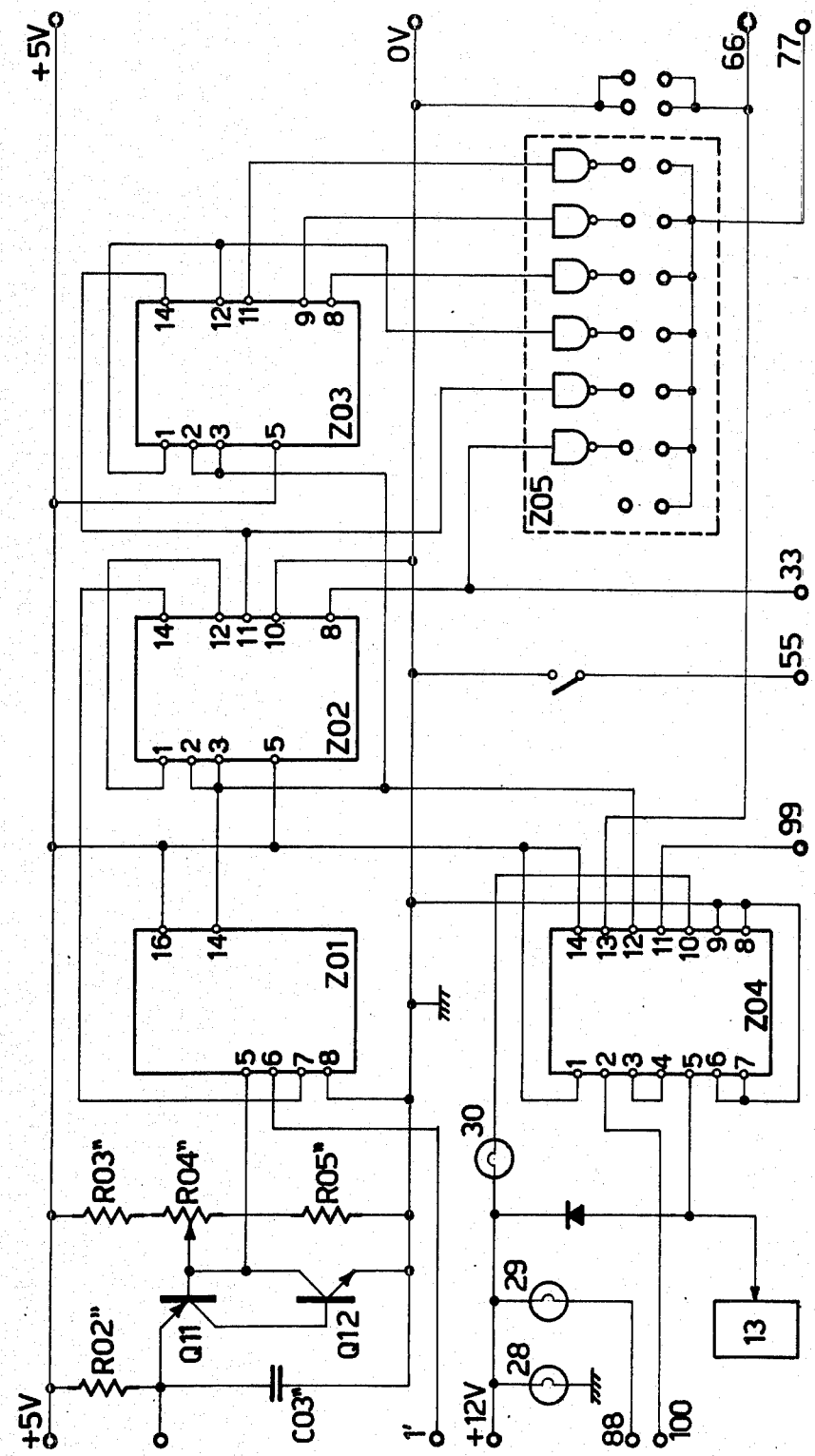
FIG. 4 diagrammatically shows timing and pre-selection circuits of the apparatus.
Figure 5:
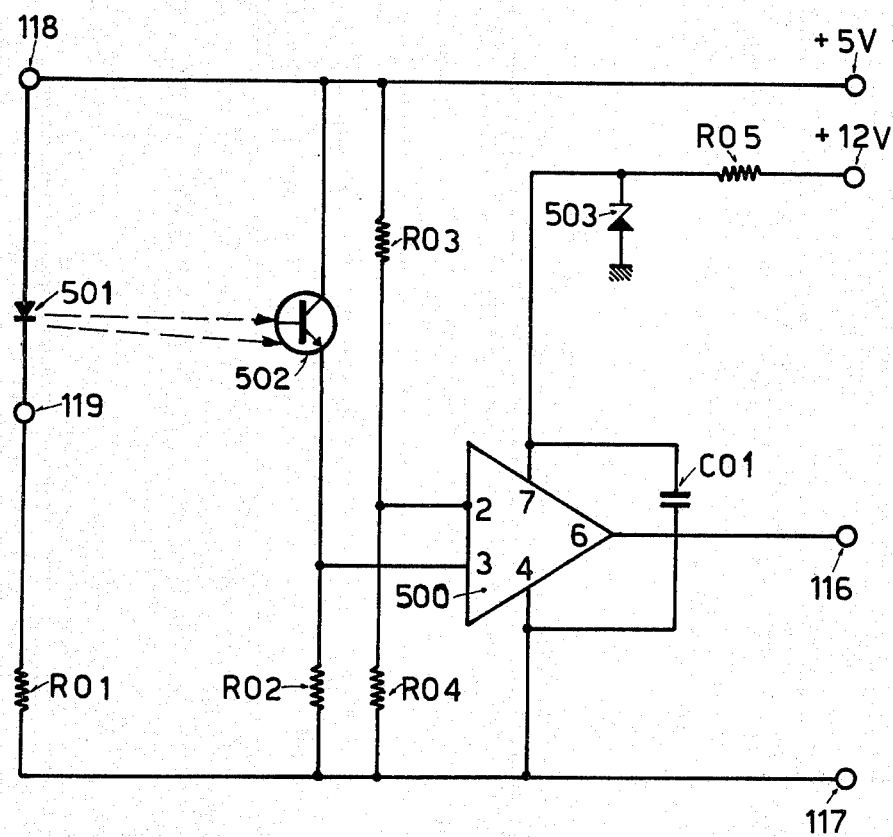
FIG. 5 diagrammatically shows a detecting circuit used by the metering apparatus.

FIGS. 3, 4 and 5 show a particularly preferred embodiment of the circuits forming the block diagram of FIG. 1.

With reference to FIG. 3, which corresponds to the blocks 6 and 13 of FIG. 1, an integrated circuit Z10 (e.g. the one produced and sold by Texas Instruments under No. SN 7493) achieves the function of dividing the frequency of the signal sent to its input 14, and another integrated circuit Z08 (for the sake of drawing clarity represented as being separated in two portions Z08a and Z08b) is provided for controlling the counting unit 25 and the actuator 7. Two flip-flops of the S-R type, formed by the NAND gates 121–123 and 141–163 are also provided.

In order to describe the operation of the circuit of FIG. 3, it is preferable to start from a situation of "reference" operation, for example from the situation obtained by positioning the slider 24 at a "stop" position. In such a condition the line 66 carries a logic zero signal and the two flip-flops are set with a logic 1 at the inputs of both NAND 121 and NAND 163. In addition, the output of NAND 142 is 1, (irrespective of the time signal on the line 1') and consequently at the output 6 of the integrated circuit Z08a (e.g the one produced and sold by Texas Instruments under No. SN 74450) there will be a logic zero, which fails to energize the drop demand actuator 7. By selecting now one of the six flowrate values for feeding the drops of liquid by moving the slider 24, the NAND 142, which is preferably a NAND gate with Schmitt trigger, will switch between logic zero and logic 1 according to the frequency signal on the line 1', e.g. 17 times per sec., since its other inputs are at logic 1 at the present flowrate.

In fact, the selection of a flow rate results in a signal of a period corresponding to the selected rate. If, for example this rate or frequency is of four drops per minute, at every 15 seconds a trailing edge is present at the input of NAND 136 and the output of NAND/123 becomes 1 (logic) due to the switching of the monostable circuit formed by a NAND gate 135, a network R07' -C04' and NAND gate with Schmitt trigger 151, as well as of the monostable circuit formed by a NAND 134, a network R08' -C05' and a NAND gate with Schmitt trigger 152. As a consequence the output of NAND switches to zero with the frequency existing on line 1, thus enabling transistor Q02, which controls the drop demand actuator 7 and a lamp 29 for signalling the drop demand (FIG. 4).

The fall of a drop, detected by the circuit of FIG. 5, as described hereafter, gives a negative pulse on the line 116, with the result that a positive pulse occurs at the collector of transistor Q01. Consequently, NAND gate 111 with Schmitt trigger having both the inputs at logic 1, switches to zero ad causes the analogous NAND 112 output to become 1, causing also the two monostable circuits formed by two triggered NAND gates 113, 114, a NAND gate 131 and two networks R04' -C02' and R05' -C03' to switch. As a result of such switching operations, the outputs of NAND gates 121, 123 and 142 become again 1, zero, 1 respectively. The output of NAND 142 being 1, stops the drop demand through the circuit Z08. If the drop demand is not satisfied, the next impulse on line 77 triggers the switching operations above described, and, due to the presence of a NAND gate 133, while the NAND 123 output being of logic 1, the output of NAND gate 162 will be zero, thus resulting in a logic 1 at the output of NAND gate 141. In this situation, periodic pulses are provided, e.g. 64 per minute, at the other input of a NAND gate with Schmitt trigger 154, a periodic logic 1 signal results on a line 99, through a NAND chain 173, 175, 174 and a resistance R09'. Line 99 controls a section of a transfer circuit Z04 for switching on an alarm lamp 30 (FIG. 4). A periodically intermittent logic 1 signal appears also on line 100 through NAND gate 173 and a pulse shaper comprised of a triggered NAND gate 153 and a network R10' -C. A line 100 controls a section of the transfer circuit Z04 (FIG. 4) for supplying power to an acoustic alarm.

NAND gate 141 can also be switched to logic 1 through a gate 164 controlled by the output 8 of the frequency divider Z10, which becomes logic 1 if there arrive eight pulses at the input 14, when the inputs 2, 3 are logic zero. This occurs if in association with a drop demand, i.e. NAND 121 output being zero and frequency divider Z10 actuated through input 2, 3, the input 14 of Z10 receives eight pulse signals through the line 33 with no drop being detected by the optic-electronic transducer of FIG. 5, causing therefore NAND 121 output to switch to logic 1.

In addition, the optic and acoustic alarm devices will be actuated through the switching to logic 1 of the gate 141 output, if a number of drops greater than one is fed in consequence of a drop demand corresponding, as already described, to the presence of a logic 1 at the output of the NAND gate 123. In fact, it is to be appreciated that the feeding of the first drop immediately switches to logic 1 the input of NAND gate 161, which is directly connected to the transistor Q01 collector, during a time interval which is the same, except for electronic delays, as the duration of the negative pulse signal at the transistor Q01 base, correlated with the detection time of the circuit of FIG. 5. If the duration time of said negative pulse signal is less than the switching time of the monostable circuits comprising NAND gates 112, 113 and 114, and the networks CO2' -R04', R05' -C03', the other input of NAND 161 connected with the NAND 121 output will become 1 only upon switching to 0 V of the voltage at the transistor Q01 collector. As a consequence, when the first drop is fed, subsequent to a drop demand, both the inputs of NAND 161 will become logic 1, but not at the same time, whereby the NAND 161 output will remain at logic 1. In the case when a drop being already fed (NAND 121 output being 1), another drop is fed without a previous demand, then both NAND 161 inputs are at logic 1 at the same time and cause NAND 161 to switch to zero with consequent switching to logic 1 of the NAND 141 output and alarm actuation.

It will be appreciated that the operation of the alarm devices is actuated by switching NAND 141 to logic 1. This switching also causes the drop feeding to stop, since at the same time the NAND 142 output will become logic 1 as a consequence of the presence of a logic zero at the output of NAND 123.

Only one exception is foreseen, which is the case where the micro flow metering apparatus is pre-set for the "draining" operation by positioning the sliding switch 24 at the corresponding position. In such operating conditions logic zero will be on the line 55, previously always at logic 1, and will continuously enable the drop demand through the transfer circuit Z08a. The alarm devices are however actuated only by the presence of a logic zero signal at the output of NAND 161 and a logic 1 signal at the output of NAND 141.

The time constants R04'-C02' and R05'-C03' should be such as to cause the NAND 121 output to switch to logic 1 and the NAND 123 output to zero upon the negative pulse on the line 116 being off. Due to the characteristics of the optic-electronic transducing circuit of FIG. 5 and the transit time of a drop within the vessel 21 (FIG. 2) these time constants should be dimensioned as follows: $C02'=22$ $\mu F$; $R04'=330\Omega$; $C03'=2,2\mu F$; $R05'=200\Omega$ The time constants R07'-C04' and R08'-C05' should be such as to ensure, at every pulse on the line 77, the NAND 123 output to switch to 1 without a contemporaneous switching to 1 of the NAND 133 output. Their dimensioning has suggested the following values: $R07'=200\Omega$; $C04'=100\mu F$; $R08'=200\Omega$ $C05'=10\mu F$;

The feeding of a drop results in the inverter 132 output switching to the logic state 1 and, through the transfer circuit Z08b, a transistor Q03 is also caused to switch on. Therefore a negative pulse appears at the Q03 collector, which triggers the counting device 25. When a drop number to be fed has been pre-set by means of the device 26 (FIGS. 1 and 2) and the switch 27 is off, as the pre-set feeding has been achieved the +112 V supply (FIG. 3) of the circuit Z08a is cut off and the actuator 7 stops its operation. Then the alarm circuits will be actuated for no drop being present during a demand period (two pulses on the line 77).

Obviously the counting device 25 allows the visualisation of the number of fed drops and is not described in details (as well as the pre-selector 26, the acoustic alarm device and actuator 7) as it is not a specific object of the invention, being available in the trade and obvious to one skilled in the art.

FIG. 5 shows a source of infra-red rays 501 (fed at d.c. voltage, e.g. 5 V between a first terminal 118 and a second terminal 119 which is connected to the ground through a resistance R01), a receiver transistor 502 and an operative amplifier 500. The receiver transistor is connected between the terminal 118 and the direct input 3 of the operative amplifier 500. The reverser input 2 of the operative amplifier 500 is connected to the terminal 118 through a resistance R03 of about 100$\Omega$ and to earth through a resistance R04 of about 400$\Omega$. The direct input terminal 3 is connected to earth through a resistance R02 of about 100 K$\Omega$. Furthermore, the operative amplifier 500 between its terminals 7 and 4 is supplied with d.c. power at a voltage regulated by a Zener diode 503. This voltage, e.g. of 12 V, is fed by a power supply connected to the diode 503 through a resistance R05. The feeding terminals 7 and 4 of the operative amplifier 500 are also mutually connected through a stabilization capacitor Co1 of about 1000 pF. The output 6 of the operative amplifier is picked out at the terminal 116.

The operation of the circuit described is extremely simple and reliable. As long as the receiver 502 receives the radiations supplied by the source 501, it will allow a current transfer between the terminal 118 and the earth 117, whereby a voltage drop across the resistance R02 will occur and the input 3 of the operative amplifier will be at a positive voltage. On the contrary, when receiver 502 is not hit by the radiations emitted by the source 501, the same receiver is off and then a voltage drop is observed at the input 3 of the amplifier, thus causing a negative pulse at the output 6 of the operative amplifier 500 (and at the terminal 116).

With further reference to FIG. 2, and in particular bearing in mind the vessel 21 of transparent material which is placed within member 23, it is clear that the radiating source 501 and the receiver 502 will be mounted on the surface encircling the vessel 21, so that the radiations emitted by the source 501 can be picked off by the receiver transistor 502. With this arrangement it is easy to understand that the negative pulse at the output terminal 116 will be obtained in consequence of the fall of a drop, because this prevents a radiation from the radiating source 501 to be picked by receiver 502.

Referring now to FIG. 4, representing the pre-selection digital circuitry, there is provided an oscillator essentially comprising two transistors Q11 and Q12, and a circuit resulting from a resistance R02" of some hundreds of K$\Omega$ and a capacitor C03" in the range of some tens of F. The oscillating frequency of the oscillator is principally given by the time constant of said RC circuit, but it can be adjusted by varying the position of the terminal which is in common both to the p-n-p transistor Q11 base and to the n-p-n transistor Q12 collector, on the bridge formed by the resistances R03", R04", R05". The oscillator output picked out at the transistor Q12 collector, is sent to the input 5 of a synchronous counter Z01, e.g. the component SN 74193, produced and sold by Texas Instrument, which on one hand sends pulses, e.g. at 17 Hz, along line 1' to input 1' of NAND gate 142, and on the other hand sends diverted pulses to a binary counter, e.g. SN 7493 of Texas Instruments.

The digital outputs 8, 11 of the second counter Z02 supply pulses of periodic frequency 64 and 32 per minute. The pulses at the output 11 of the counter Z02 are sent to the input 14 of another binary counter Z03, e.g. again SN 7493 of Texas Instruments, which supplies, after a subsequent division of the frequency received, pulses of periodic frequencies 16,8,4 and 2 per minute, at its outputs 12,9,8 and 11 respectively.

The six frequencies thus obtained are supplied across the line 77, through an inverter circuit Z05 formed of the NAND gates, upon selection by means of the slider switch 24 (FIG. 2), whereby the positioning of the switch 24 allows the choice of one of these frequencies. The "stop" position of the slider switch 24 gives a logic state 0 at the input 13 of a transfer circuit Z04 (e.g. SN 754504 of Texas Instruments), which causes the counters Z01, Z02, Z03 to stop, by means of the output 12 to Z04. The circuitry of FIG. 4 is not described in more detail as it is designed according to conventional arrangements known to those skilled in the art. The connections between the circuits of FIGS, 3,4 and 5 are indicated by identical reference numerals.

It is obvious that the micro-flow metering apparatus of the invention will be also provided with a suitable power circuit, for ensuring its operation by both batteries and mains voltage, being adapted to supply regulated voltages. e.g. at 5 V and 12 V. This power circuit will not be described herein.

What I claim is:

1. A metering apparatus for a liquid adapted to be placed between a liquid feeding container and a flow delivery line, comprising: an actuator for delivering liquid drops from the feeding container to the flow delivery line; a counting circuit, means for presetting said counting circuit to a desired flow rate of liquid drops deliverable to the flow delivery line, a control apparatus including a sequential circuit having an input coupled to said counting circuit and an output coupled to said actuator for controlling said actuator to deliver liquid drops, according to the preset rate, to the delivery line; means at the output of the metering apparatus for electronically sensing the actual delivered drops and providing an output proportional to the rate of drops actually delivered to the flow delivery line, said output being coupled to said sequential circuit and alarm means coupled to said sequential circuit and operable to cause an alarm in response to sensing a disparity between the rate of the drops delivered and the drop rate preset by said counting circuit, said counting circuit including an oscillator providing an output signal, a plurality of digital counters connected as frequency dividers for the output signal of the oscillator and a plurality of inverters connected to some outputs of the counters, a slider for presetting the delivery flow rate of the metering apparatus and connecting one of the outputs of the inverters to an input of the control apparatus, the two outputs of said counters having the highest frequencies being directly connected with two corresponding inputs of the control apparatus in order to clock the sequential circuit.

2. Apparatus as claimed in claim 1 wherein said sequential circuit comprises two flip-flops of the S-R type, a frequency divider and a plurality of monostable circuits (one-shots), one of the flip-flops being connected on the one hand to a chain of monostable circuits receiving at its input from the counting circuit the frequency preset as delivery frequency, and on the other hand to a second chain of monostable circuits receiving at its input a signal from said electronic sensing means the second of the two flip-flops having as input the outputs of three NAND gates, the first of which has one input connected to said electronic sensing means and a second input connected to the direct output of said first flip-flop; the second NAND gate having one input connected to the second chain of monostable circuits and a second input connected to the reverse output of said first flip-flop; and the third NAND gate being an inverter having its input connected to one of the outputs of said frequency divider, which is controlled by one of the higher frequency outputs of one of the counters of the counting circuit and enabled by the direct output of the first flip-flop.

3. Apparatus according to claim 2, in which the first flip-flop enables a drop delivery upon the preset frequency, the second flip-flop of the sequential circuit being connected to said alarm means which is enabled by means of the first NAND gate if more drops are sensed than the required number, by means of the second NAND gate if the absence of a drop delivered in response to a drop demand is sensed, and by means of the third NAND gate if a drop is delivered with delay upon a drop demand, the output of the second flip-flop being connected for preventing when set, the output of the first flip-flop from demanding a drop delivery.

4. A metering apparatus for a liquid adapted to be placed between the liquid feeding container and a flow delivery line, comprising: an actuator for delivering liquid drops from the feeding container to the flow delivery line; a counting circuit, means for presetting said counting circuit to a desired flow rate of liquid drops deliverable to the flow delivery line, a control apparatus including a sequential circuit having an input coupled to said counting circuit and an output coupled to said actuator for controlling said actuator to deliver liquid drops, according to the preset rate, to the delivery line; means at the output of the metering apparatus for electronicaly sensing the actual delivered drops and providing an output proportional to the rate of drops actually delivered to the flow delivery line, said output being coupled to said sequential circuit; alarm means coupled to said sequential circuit and operable to cause an alarm in response to sensing a disparity between the rate of the drops delivered and the drop rate preset by said counting circuit; a resettable counter, and means connecting said resettable counter to an output of said sequential circuit to count the drops acutually delivered to the flow delivery line.

5. Apparatus according to claim 4 including a device for selecting the total number of drops to be delivered, means coupling said device and said resettable counter for comparing the total number of drops to be delivered and the actual number of drops delivered responsive to the coincidence thereof to disable said actuator and stop delivery of further drops.

* * * * *

UNITED STATES PATENT AND TRADEMARK OFFICE
CERTIFICATE OF CORRECTION

PATENT NO. : 4,001,801
DATED : January 4, 1977
INVENTOR(S) : Camille Moulet

It is certified that error appears in the above-identified patent and that said Letters Patent are hereby corrected as shown below:

Column 7, line 50, in claim 2, after "means" insert --,--.

Signed and Sealed this

Twenty-ninth Day of March 1977

[SEAL]

Attest:

RUTH C. MASON
*Attesting Officer*

C. MARSHALL DANN
*Commissioner of Patents and Trademarks*